US012569163B2

(12) United States Patent (10) Patent No.: US 12,569,163 B2

Hu et al. (45) Date of Patent: Mar. 10, 2026

(54) SYSTEM OF MEASURING EXHALATION METABOLISM

(71) Applicant: Research Center for Eco-Environmental Sciences, Chinese Academay of Sciences, Beijing (CN)

(72) Inventors: Ligang Hu, Beijing (CN); Chen Tao, Beijing (CN); Guibin Jiang, Beijing (CN)

(73) Assignee: Research Center for Eco-Environmental Sciences, Chinese Academy of Sciences, Beijing (CN)

( * ) Notice: Subject to any disclaimer, the term of this patent is extended or adjusted under 35 U.S.C. 154(b) by 454 days.

(21) Appl. No.: 18/547,739

(22) PCT Filed: Feb. 25, 2021

(86) PCT No.: PCT/CN2021/077865

§ 371 (c)(1),
(2) Date: Oct. 10, 2023

(87) PCT Pub. No.: WO2022/178752

PCT Pub. Date: Sep. 1, 2022

(65) Prior Publication Data

US 2024/0180444 A1 Jun. 6, 2024

(51) Int. Cl.
*A61B 5/083* (2006.01)
*A61B 5/113* (2006.01)
(Continued)

(52) U.S. Cl.
CPC .............. *A61B 5/083* (2013.01); *A61B 5/113* (2013.01); *G01N 1/34* (2013.01); *G01N 1/405* (2013.01);
(Continued)

(58) Field of Classification Search
CPC ...... A61B 5/083; A61B 5/0833; A61B 5/0836
See application file for complete search history.

(56) References Cited

U.S. PATENT DOCUMENTS

2012/0294876 A1 11/2012 Zimmerman

FOREIGN PATENT DOCUMENTS

CN 201426710 Y 3/2010
CN 102389339 A 3/2012
(Continued)

OTHER PUBLICATIONS

Gao et al., Animal Breath Collecting Device, May 2018, Espacenet Machine Translation (Year: 2018).*

(Continued)

*Primary Examiner* — Erika J. Villaluna
(74) *Attorney, Agent, or Firm* — Westman, Champlin & Koehler, P.A.

(57) ABSTRACT

Provided is a system of measuring exhalation metabolism, in which: a first end of an air pump is connected to an outlet of an organic steam micro-injection module, and a second end of the air pump is connected to a first end of a liner; an air outlet of an individual exhalation imprinting sampling module is connected to a second end of the liner, and a stirrer adsorption extraction rod is provided inside the liner to sample an exhalation metabolite of an experimental animal; the air outlet of the individual exhalation imprinting sampling module is connected to a nozzle interface of an aerosol nozzle, while an air inlet thereof is connected to an air outlet of a zero-level air purifier. The system further includes a gas solenoid valve and an automatic solvent desorption module.

10 Claims, 11 Drawing Sheets

(51) Int. Cl.
    *G01N 1/34*         (2006.01)
    *G01N 1/40*         (2006.01)
    *G01N 33/497*     (2006.01)

(52) U.S. Cl.
    CPC ........ *G01N 33/497* (2013.01); *A61B 2503/40* (2013.01); *A61B 2503/42* (2013.01); *G01N 33/4975* (2024.05)

(56) References Cited

FOREIGN PATENT DOCUMENTS

| CN | 203988482 | U | 12/2014 |
|---|---|---|---|
| CN | 104367398 | A | 2/2015 |
| CN | 105796105 | A | 7/2016 |
| CN | 106175975 | A | 12/2016 |
| CN | 207366281 | U | 5/2018 |
| CN | 208447842 | U | 2/2019 |
| CN | 109745142 | A * | 5/2019 |
| CN | 110269721 | A | 9/2019 |
| JP | 2005257373 | A | 9/2005 |
| WO | 2009106349 | A1 | 9/2009 |
| WO | 2010002331 | A1 | 1/2010 |
| WO | 2015125323 | A1 | 8/2015 |
| WO | 2018235735 | A1 | 12/2018 |

OTHER PUBLICATIONS

Gu et al., A Breathing Device for Exposing and for Respiratory Administration by Respiratory Exposure System, Feb. 2019, Espacenet Machine Translation (Year: 2019).*
International Search Report and Written Opinion for International Application No. PCT/CN2021/077865, dated Nov. 24, 2021, 12 pages.
First Office Action, including Search Report, for Chinese Patent Application No. 202110213588.9, dated Nov. 25, 2021, 10 pages.

* cited by examiner

SYSTEM OF MEASURING EXHALATION METABOLISM

CROSS REFERENCE TO RELATED APPLICATIONS

This application is a Section 371 National Stage Application of International Application No. PCT/CN2021/077865, filed on Feb. 25, 2021, and published as WO/2022/178752 A1, on Sep. 1, 2022, not in English, the whole disclosure of which is incorporated herein by reference in its entirety.

TECHNICAL FIELD

The present disclosure relates to the field of biological experiment, and in particular, to a system of measuring exhalation metabolism.

BACKGROUND

In a traditional exhalation metabolome research and other metabolome researches, a metabolism at a time-point after an inhalation exposure has already been able to be detected. However, at present, there is still a lack of a technology combining inhalation exposure and exhalation imprinting in real time.

In researches of biology, medicine, pharmacy and other fields, a real-time response of an exhalation metabolome change to the inhalation exposure plays an irreplaceable role in revealing an immediate health effect of an exogenous substance entering an organism through inhalation.

Therefore, it is urgent to provide a system of measuring exhalation metabolism combining natural inhalation exposure with exhalation imprinting technology in real time.

SUMMARY

(I) Technical Problems to be Solved

The present disclosure provides a system of measuring an exhalation metabolism, so as to solve the above-mentioned technical problems.

(II) Technical Solutions

According to an aspect of the present disclosure, a system of measuring exhalation metabolism is provided, comprising: an organic steam micro-injection module, an organic steam is output from an outlet of the organic steam micro-injection module; an air pump, a first end of the air pump is connected to the outlet of the organic steam micro-injection module, and a second end of the air pump is connected to a first end of a liner; an individual exhalation imprinting sampling module, an experimental animal is placed inside the individual exhalation imprinting sampling module, an air outlet of the individual exhalation imprinting sampling module is connected to a second end of the liner, and a stirrer adsorption extraction rod is provided inside the liner to sample an exhalation metabolite of the experimental animal; an aerosol nozzle radially provided with at least one nozzle interface, the nozzle interface is connected to the air outlet of the individual exhalation imprinting sampling module; a gas solenoid valve connected to a first end of the aerosol nozzle; a zero-level air purifier, an air outlet of the zero-level air purifier is connected to an air inlet interface of the gas solenoid valve and/or an air inlet of the individual exhalation imprinting sampling module; the gas solenoid valve is configured to control zero-level air output by the zero-level air purifier to enter the individual exhalation imprinting sampling module and synchronously block an inhaled exposed substance from entering the individual exhalation imprinting sampling module; and an automatic solvent desorption module configured to detect the exhalation metabolite collected by the stirrer adsorption extraction rod.

In some embodiments of the present disclosure, the system further includes: an external standard module connected to the second end of the liner, the external standard module is configured to simulate an exhalation process of the experimental animal and an external standard quantification of a target metabolite; an organic steam interface of the external standard module is connected to the air outlet of the zero-level air purifier.

In some embodiments of the present disclosure, the system further includes: an air background module connected to the second end of the liner, the air background module is configured to detect an air background in the system of measuring exhalation metabolism.

In some embodiments of the present disclosure, the individual exhalation imprinting sampling module comprises: a mask, a cross section of the mask has a double-layer lumen structure; the air inlet in communication with a first end of an inner lumen tube of the mask; the air outlet in communicated with an outer wall surface of an outer lumen tube of the mask; an experimental animal oro-nasal interface, a first end of the experimental animal oro-nasal interface is connected to a second end of the mask; a head of the experimental animal extends into a second end of the experimental animal oro-nasal interface and is opposite to a second end of the inner lumen of the mask; a main pipe, a first end of the main pipe is spliced with the second end of the mask; and a hygroscopic strip plate, a first end of the hygroscopic strip plate is spliced with the first end of the main pipe, a second end of the hygroscopic strip plate is connected to a second end of the main pipe through a limit baffle, and the hygroscopic strip plate is opposite to a ventral surface of the experimental animal.

In some embodiments of the present disclosure, the main pipe and the hygroscopic strip plate have a transparent structure, and the individual exhalation imprinting sampling module further comprises: a camera fixing ring sleeved on an outer wall of the main pipe; a camera connected to the camera fixing ring, a lens of the camera is opposite to the ventral surface of the experimental animal; and an exhalation video collector configured to receive a breath video of the experimental animal shot by the camera.

In some embodiments of the present disclosure, the system further includes: a multifunctional ejector, a first end of the multifunctional ejector is connected to a second end of the aerosol nozzle, and a second end of the multifunctional ejector is connected to the air outlet of the zero-level air purifier; the multifunctional ejector comprises: an ejector chamber connected to a first end of a gas-liquid interface; the gas-liquid interface, a second end of the gas-liquid interface is connected to the organic steam micro-injection module; a two-phase nozzle, a first end of the two-phase nozzle extends into the ejector chamber, a second end of the two-phase nozzle is connected to the air outlet of the zero-level air purifier, and the two-phase nozzle is configured to pneumatically atomize a liquid in the ejector chamber and generate an aerosol; and a turbulence cone disposed inside the ejector chamber, the turbulence cone is disposed opposite to the first end of the two-phase nozzle so as to impact the aerosol inside the ejector chamber.

In some embodiments of the present disclosure, the organic steam micro-injection module comprises: an injector, a cavity of the injector is filled with the organic steam; a thermostatic slot seat, the injector is inserted into a slot body of the thermostatic slot seat; a guide rod, a push rod is fixed on the thermostatic slot seat; a stress plate sleeved on the guide rod; and a drive device configured to drive the stress plate to move along the guide rod toward the thermostatic slot seat, the stress plate is configured to press the push rod of the injector, so that the organic steam is output through an injection port of the injector.

In some embodiments of the present disclosure, the system further includes: an exhalation imprinting operation cabin configured to accommodate the air pump, the individual exhalation imprinting sampling module, the aerosol nozzle and the gas solenoid valve; the exhalation imprinting operation cabin comprises: a top cover, the air pump penetrates the top cover and is connected to the outlet of the organic steam micro-injection module; a bottom cover, a second end of the aerosol nozzle penetrates the bottom cover, the top cover and the bottom cover are embedded with an inner track and an outer track; two curved sliding doors respectively disposed between the top cover and the bottom cover, the two curved sliding doors slide along the inner track and the outer track through a roller, respectively; a support frame, two ends of the support frame are connected to the top cover and the bottom cover, respectively; and a support disk disposed between the top cover and the bottom cover, the support disk penetrates the support frame.

In some embodiments of the present disclosure, the automatic solvent desorption module comprises: an accommodating cavity, two smooth electromagnetic rods and a transmission rubber rod, the transmission rubber rod is disposed between the two smooth electromagnetic rods, and two ends of the transmission rubber rod and the smooth electromagnetic rod penetrate the accommodating cavity, respectively; a sample bottle horizontally placed between the two smooth electromagnetic rods, a solvent and the stirrer adsorption extraction rod are provided inside the sample bottle, and the stirrer adsorption extraction rod is provided with a magnetic core; a stepping motor configured to electromagnetically drive the smooth electromagnetic rod to rotate; and a desorption process controller configured to control a rotation direction, a rotation speed and rotation time of the sample bottle.

In some embodiments of the present disclosure, the automatic solvent desorption module further comprises: a sample bottle magnetic pipe rack configured to vertically insert the desorbed sample bottle into the sample bottle magnetic pipe rack; two ends of each sample bottle magnetic pipe rack are provided with magnetic fields with opposite magnetic field directions, so that the stirrer adsorption extraction rod inside the sample bottle is attached to an inner wall of the sample bottle.

(III) Advantages

It can be seen from the above-mentioned technical solutions that the system of measuring exhalation metabolism in the present disclosure has at least one or part of the following advantages:

(1) The system of measuring exhalation metabolism provided by the present disclosure may realize a synchronous operation of inhalation exposure and exhalation imprinting on the experimental animal.

(2) The setting of the external standard module in the present disclosure may simulate the exhalation process of the experimental animal and the external standard quantification of the target metabolite, which may facilitate a targeting research.

(3) The setting of the air background module in the present disclosure may detect the air background in an exhalation metabolic system, which may play an important role in studying an influence of the air background on the exhalation metabolic system.

(4) The setting of the hygroscopic strip plate in the individual exhalation imprinting sampling module in the present disclosure may prevent metabolites in exhaled air of the experimental animal entering a carrier from being disturbed by excretory substances, i.e., feces and urine.

(5) In the present disclosure, an open and transparent design of the individual exhalation imprinting sampling module for a thoracico-ventral region of the experimental animal combined with a breath video collection may provide a non-closed and relatively friendly breath physiological monitoring environment for the experimental animal.

(6) A combined use of the multifunctional ejector and the organic steam micro-injection module in the present disclosure may support an inhalation exposure operation of mixed gas, liquid aerosol and organic steam to the experimental animal.

(7) The exhalation imprinting operation cabin in the present disclosure may be opened at any angle, which is more convenient for the experimental operation.

(8) The automatic solvent desorption module in the present disclosure keeps a solvent desorption operation process consistent, which may ensure a relatively stable desorption efficiency, and provide convenience for a sample pretreatment during an off-line detection.

DETAILED DESCRIPTION OF EMBODIMENTS

Figure 1:
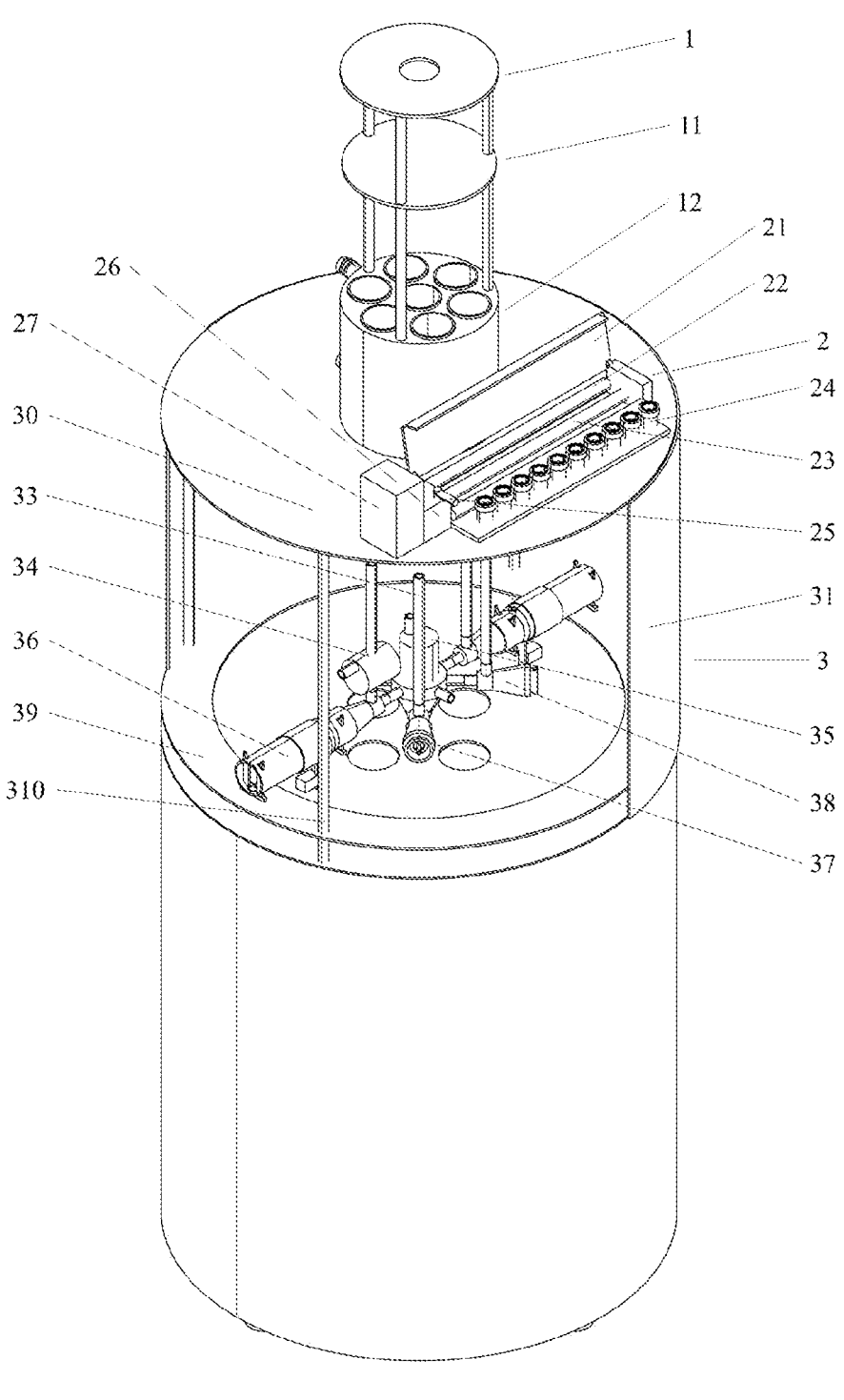
FIG. 1 is a schematic diagram of a system of measuring exhalation metabolism according to embodiments of the present disclosure.
Figure 2:
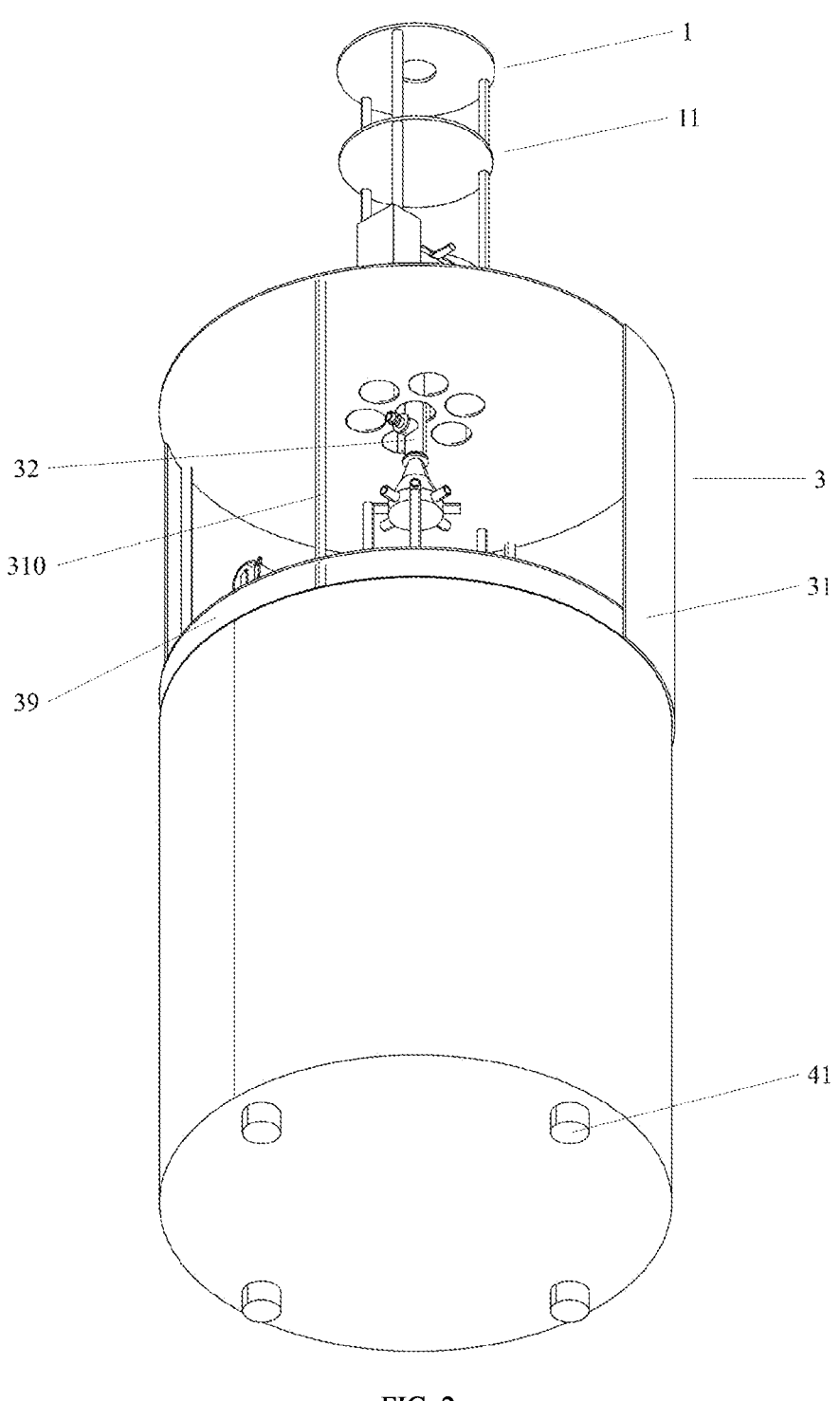
FIG. 2 is a schematic diagram from another perspective of a system of measuring exhalation metabolism according to embodiments of the present disclosure.
Figure 3:
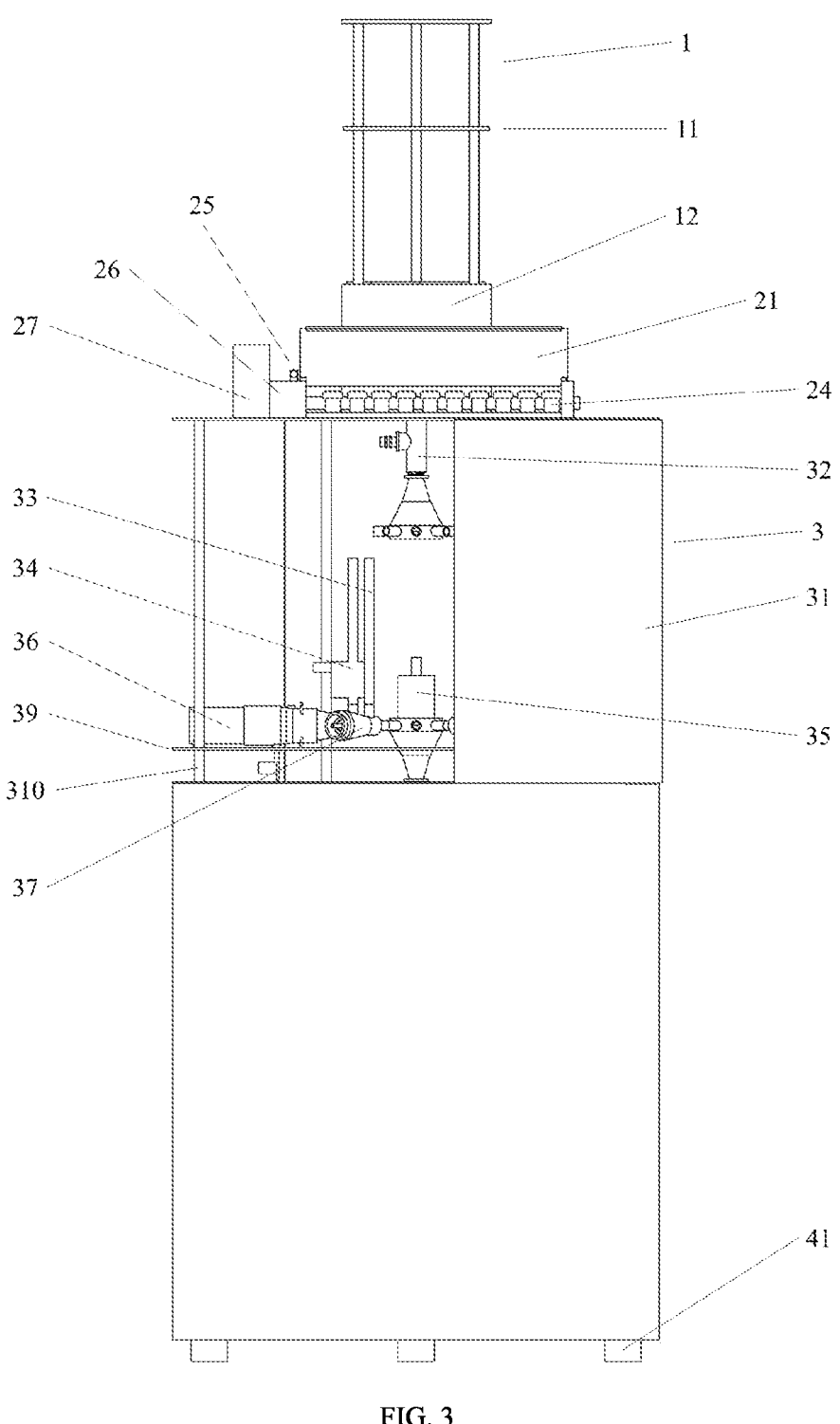
FIG. 3 is a schematic front view of a system of measuring exhalation metabolism according to embodiments of the present disclosure.
Figure 4:
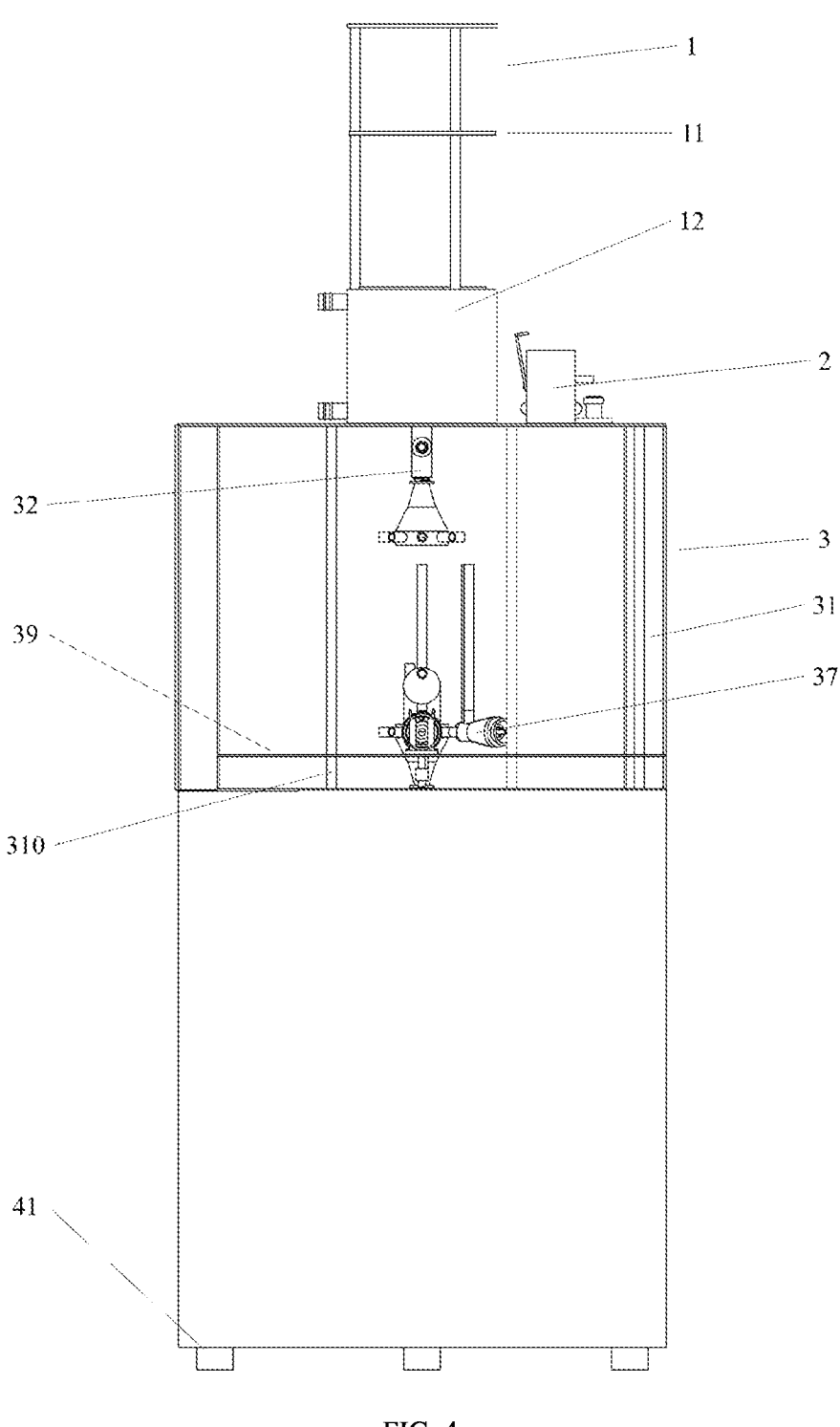
FIG. 4 is a schematic side view of a system of measuring exhalation metabolism according to embodiments of the present disclosure.
Figure 5:
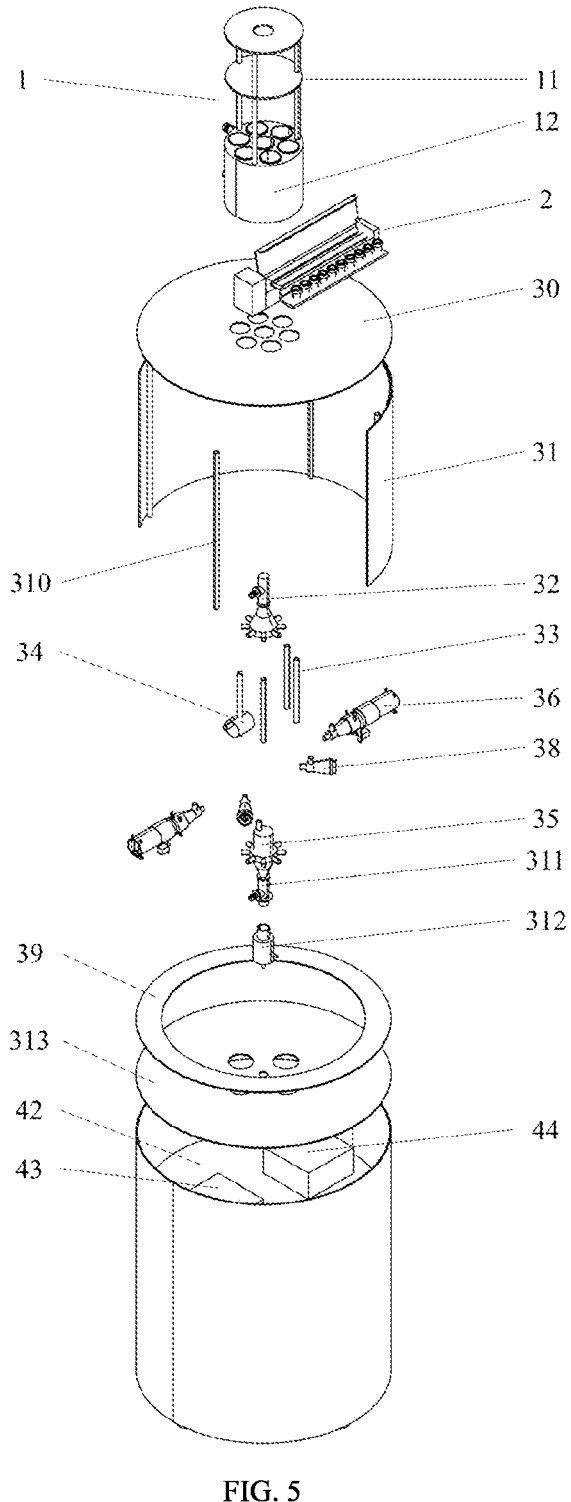
FIG. 5 is a disassembled schematic diagram of a structure of FIG. 1.
Figure 6:
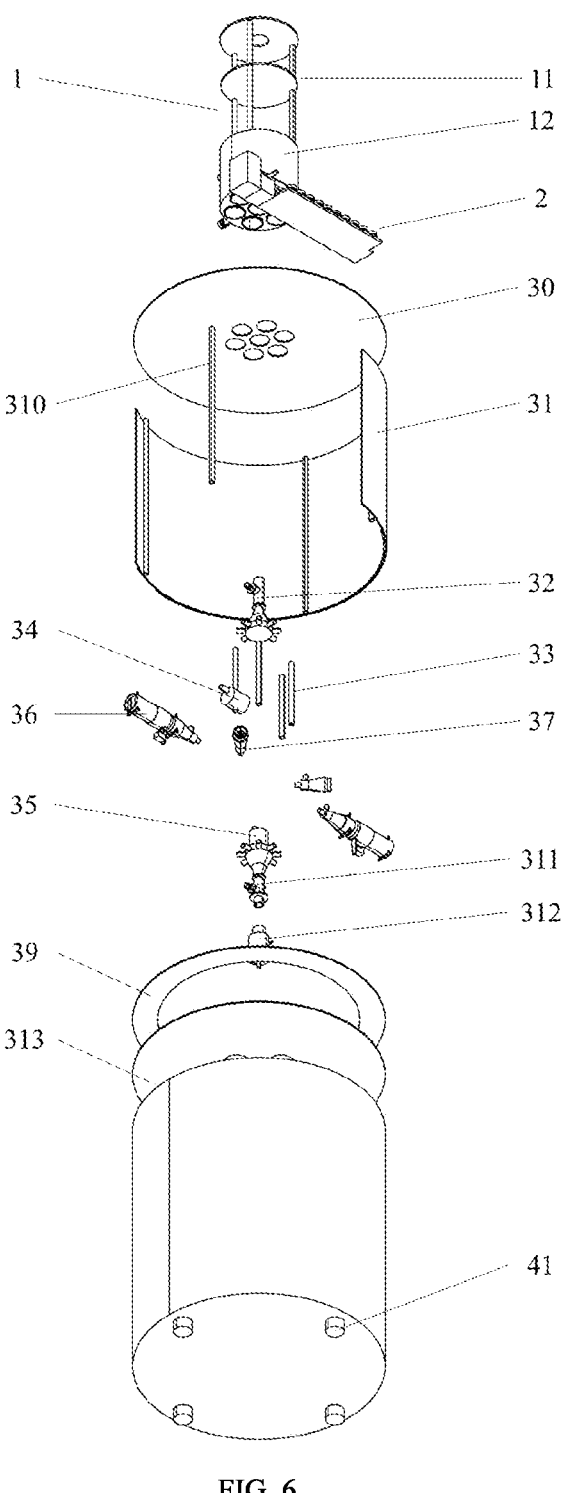
FIG. 6 is a disassembled schematic diagram of a structure of FIG. 2.
Figure 7:
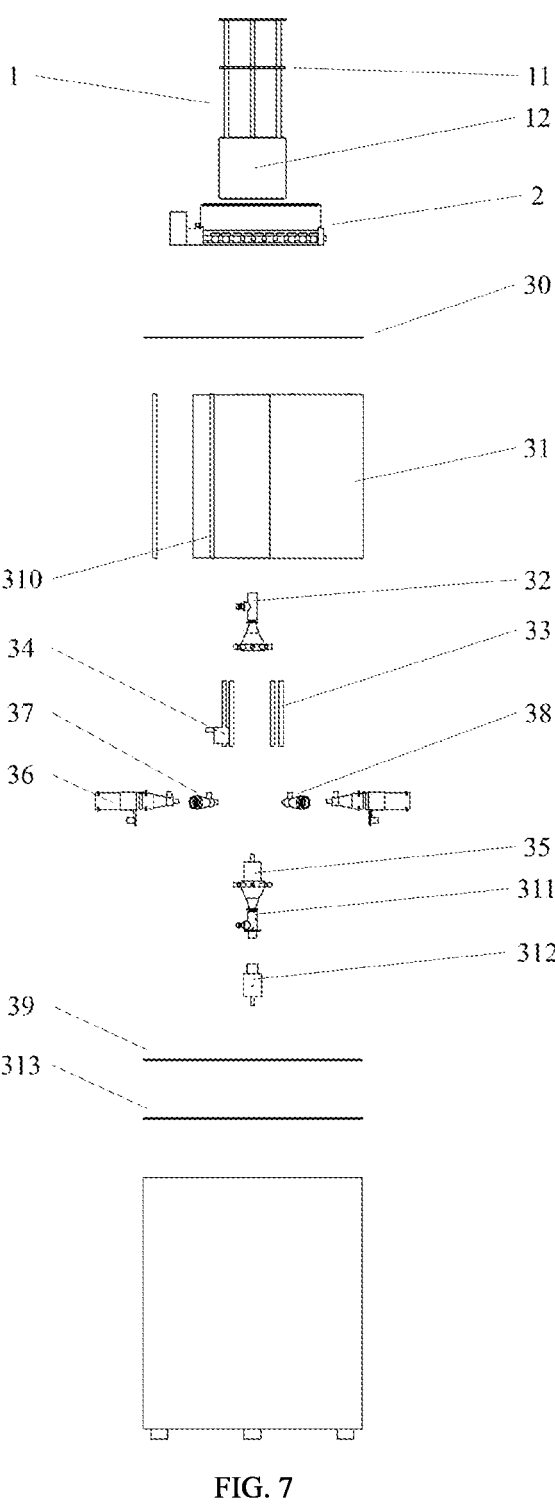
FIG. 7 is a disassembled schematic diagram of a structure of FIG. 3.
Figure 8:
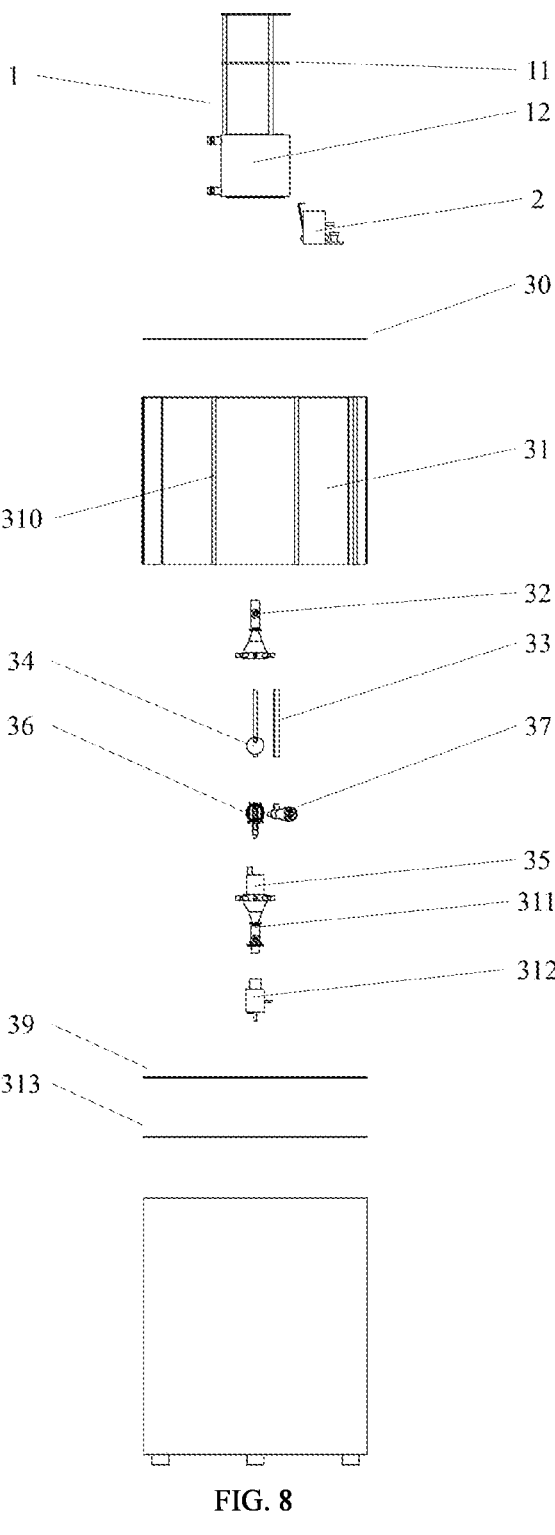
FIG. 8 is a disassembled schematic diagram of a structure of FIG. 4.

The present disclosure provides a system of measuring exhalation metabolism, including: an organic steam micro-injection module, an air pump, an individual exhalation imprint sampling module, an aerosol nozzle, a gas solenoid valve, a zero-level air purifier and an automatic solvent desorption module. A first end of the air pump is connected to an outlet of the organic steam micro-injection module, and a second end of the air pump is connected to a first end of a liner. An air outlet of the individual exhalation imprint sampling module is connected to a second end of the liner, and a stirrer adsorption extraction rod is provided inside the liner to sample an exhalation metabolite of an experimental animal. The air outlet of the individual exhalation imprint sampling module is connected to a nozzle interface of the aerosol nozzle, and an air inlet of the individual exhalation imprint sampling module is connected to an air outlet of the zero-level air purifier. The gas solenoid valve is used to control zero-level air to enter the individual exhalation imprint sampling module and synchronously block an inhaled exposed substance from entering the individual exhalation imprint sampling module. The automatic solvent desorption module is used to detect the exhalation metabolite collected by the stirrer adsorption extraction rod. The present disclosure may realize a synchronous operation of inhalation exposure and exhalation imprint on the experimental animal.

In order to make objectives, technical solutions and advantages of the present disclosure clearer, the present disclosure will be further described in detail below with reference to specific embodiments and accompanying drawings.

Some embodiments of the present disclosure will be described more comprehensively below with reference to the accompany drawings, some but not all of which will be shown. In fact, various embodiments of the present disclosure may be implemented in many different forms and should not be construed as limiting the embodiments described here. Rather, these embodiments are provided so that the present disclosure may satisfy applicable legal requirements.

It is helpful to define some specific words before describing the solution to the problem.

The "inhalation exposure" described herein refers to a process that a substance in an inhalation exposure pathway naturally or artificially forms an aerosol and is input to an organism through a respiratory tract during a natural breath of a living body.

The "exhalation imprinting" described herein refers to a collection and detection of a metabolite (e.g., a volatile organic compound) contained in an exhaled aerosol, that is, a sampling and detection process in the exhalation metabolome research.

A research object of metabolomics is an endogenous metabolite (metabolic intermediate or end product). By analyzing a change rule of these metabolites in body fluids and tissues, an influence of internal and external factors such as a gene expression, a protein regulation, etc. on an organism status may be analyzed from a whole organism. Any change of physiological, pathological or other factors in the organism may affect a concentration of metabolites or change a metabolic flow, thus a metabolomics technology may reflect an actual situation of the organism more truly. The metabolomes may be divided into blood metabolome, tissue metabolome, urine metabolome, exhalation metabolome, etc. according to sample sources of the metabolites.

Among many metabolome studies, the exhalation metabolome has characteristics of continuous, noninvasive and convenient sampling. Substances discharged directly from a blood-air barrier or a respiratory tract are mixed with air to form an aerosol, including an endogenous volatile organic compound, a nonvolatile organic compound, an inorganic gas, etc. The endogenous volatile organic compound is a most studied substance in the exhalation metabolome. Comparing a difference between sampling methods determined by sample sources in different metabolome studies, the exhalation metabolome research has an advantage of continuous sampling. Based on a semi-permeability of a blood-gas barrier of the organism, a considerable gas-liquid exchange area during breath, a water vapor evaporation and a pneumatic atomization of a liquid film on an inner surface of a lower respiratory tract (including a bronchiole, a respiratory bronchiole, an alveolar duct, etc.), the exhalation metabolome may not only reflect metabolism of respiratory related tissues, but also reflect secondary and systemic metabolism by presenting metabolites in blood.

In a first exemplary embodiment of the present disclosure, there is provided a system of measuring exhalation metabolism. As shown in FIG. 1 to FIG. 8, before describing the first exemplary embodiment of the present disclosure in detail, it should be noted in advance that a first end to a second end is from top to bottom in a vertical direction and from right to left in a horizontal direction.

The system of measuring exhalation metabolism according to the present disclosure includes: an organic steam micro-injection module 1, an air pump 32, an individual exhalation imprinting sampling module 36, an aerosol nozzle 311, a gas solenoid valve 35, a zero-level air purifier 42, and an automatic solvent desorption module 2.

Figure 13:
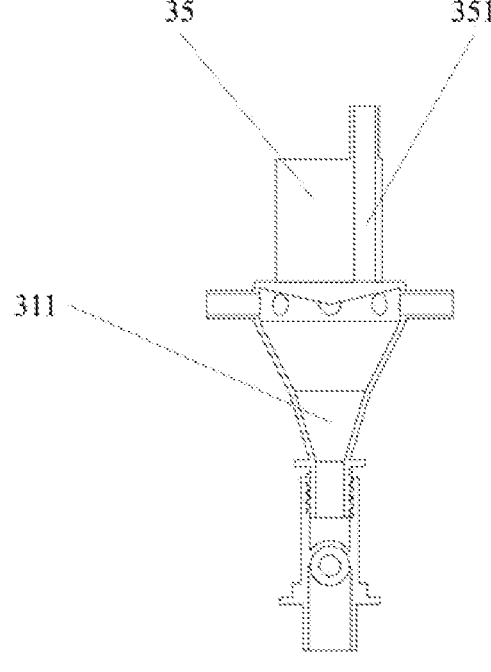
FIG. 13 is a schematic structural diagram of a gas solenoid valve.

A first end of the air pump 32 is connected to an outlet of the organic steam micro-injection module 1, and the outlet of the organic steam micro-injection module 1 outputs an organic steam. A second end of the air pump 32 is connected to a first end of the liner 33. An air outlet of the individual exhalation imprinting sampling module 36 is connected to a second end of the liner 33, the air outlet of the individual exhalation imprinting sampling module 36 is connected to a nozzle interface of the aerosol nozzle 311, and an air inlet of the individual exhalation imprinting sampling module 36 is connected to an air outlet of the zero-level air purifier 42. The liner 33 is further provided with a gas shunting solenoid valve 34. The gas solenoid valve 35 is connected to a first end of the aerosol nozzle 311. As shown in FIG. 13, an air inlet interface 351 of the gas solenoid valve 35 is connected to the zero-level air purifier 42, and the gas solenoid valve is used to control zero-level air to enter the individual exhalation imprinting sampling module 36 and synchronously block an inhaled exposed substance from entering the individual exhalation imprinting sampling module 36. A stirrer adsorption extraction rod is provided inside the liner 33 to sample an exhalation metabolite of an experimental animal, and then the automatic solvent desorption module 2 is used to detect the exhalation metabolite collected by the stirrer adsorption extraction rod.

Components of the system of measuring exhalation metabolism will be described in detail below.

The organic steam micro-injection module 1 includes: an injector, a thermostatic slot seat 12, a guide rod, a stress plate 11 and a drive device. The injector is inserted into a slot body of the thermostatic slot seat 12, a cavity of the injector is filled with the organic steam, and the thermostatic slot seat 12 has a function of a thermal insulation and promoting evaporation of the organic steam inside the cavity of the injector. The guide rod is fixed on the thermostatic slot seat 12, and the stress plate 11 is sleeved on the guide rod. The drive device drives the stress plate 11 to move along the guide rod toward the thermostatic slot seat 12, and the stress plate 11 presses a push rod of the injector, so that the organic steam is output through an injection port of the injector. When the organic steam is prepared, the zero-level air purifier 42 is docked with the cavity of the injector to provide pure air therefor. A hydraulic push rod, or a mechanical push rod of a stepping motor may be selected as the drive device. A bottom portion of the zero-level air purifier 42 is provided with a vibration-damping foot column 41 so as to reduce a mechanical vibration when the zero-level air purifier 42 is operating.

Figure 9:
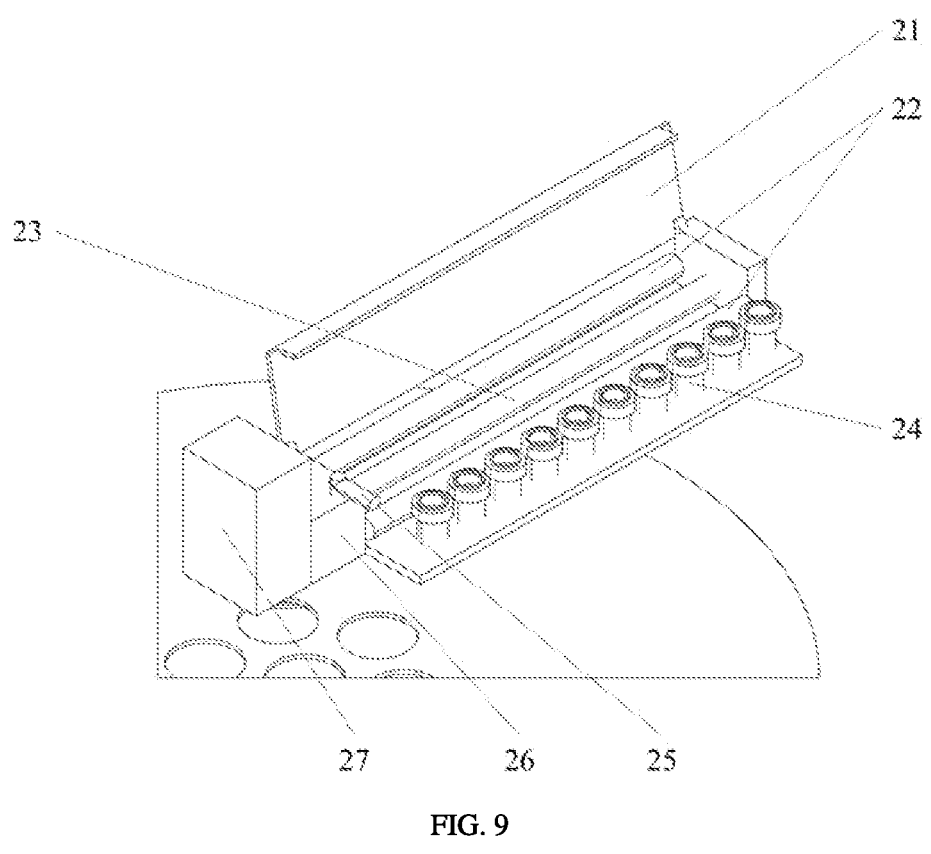
FIG. 9 is a partial enlarged view of an automatic solvent desorption module in FIG. 1.

As shown in FIG. 9, the automatic solvent desorption module 2 includes: an accommodating cavity, a cover 21, a cover buckle 25, two smooth electromagnetic rods 22, a transmission rubber rod 23, a sample bottle, a sample bottle magnetic pipe rack 24, a stepping motor 26 and a desorption process controller 27. The transmission rubber rod 23 is disposed between the two smooth electromagnetic rods 22, and two ends of the transmission rubber rod 23 and the smooth electromagnetic rod 22 are respectively connected to a wall surface of the accommodating cavity. The sample bottle is horizontally placed between the two smooth elec-tromagnetic rods 22, a solvent and the stirrer adsorption extraction rod are provided inside the sample bottle, and the stirrer adsorption extraction rod is provided with a magnetic core. The stepping motor 26 electromagnetically drives the smooth electromagnetic rod 22 to rotate. The desorption process controller 27 controls a rotation direction, a rotation speed and rotation time of the sample bottle.

The sample bottle provided with the solvent and the stirrer adsorption extraction rod (with the magnetic core) is hori-zontally placed between the smooth electromagnetic rod 22 and the transmission rubber rod 23. Before starting an automatic solvent desorption, a direction of the sample bottle is adjusted so that a magnetic field direction of the magnetic core may be the same as a magnetic field direction of the electrified smooth electromagnetic rod 22. When the cover 21 and the cover buckle 25 are closed, the stirrer adsorption extraction rod bounces up and leaves the solvent. The transmission rubber rod 23 makes the sample bottle roll continuously by friction, and the stirrer adsorption extrac-tion rod is constantly soaked by the solvent. The smooth electromagnetic rod 22 is not energized during a rolling process of the sample bottle and only plays a supporting role. The stepping motor 26 drives the transmission rubber rod 23 to rotate, and the rotation direction, the rotation speed and the rotation time of the transmission rubber rod 23 are adjusted by the desorption process controller 27. When the rotation is finished, the desorption process controller 27 automatically turns on a power source of the smooth elec-tromagnetic rod 22, and the stirrer adsorption extraction rod bounces up, and the automatic desorption process ends. Two sides of each sample bottle magnetic pipe rack 24 are provided with magnets with opposite magnetic field direc-tions, so it is not required to adjust a direction of the stirrer adsorption extraction rod (with the magnetic core) in the sample bottle. When the sample bottle after finishing the desorption process is inserted into the sample bottle mag-netic pipe rack 24, the stirrer adsorption extraction rod in the sample bottle is attached to an inner wall of the bottle, which may facilitate transferring the desorbed solution from a bottle mouth by a pipette. A gas flow controller 43 is selected to control a gas flow rate of the above-mentioned gas path portion.

In alternative embodiments, the system of measuring exhalation metabolism further includes: an exhalation imprinting operation cabin 3 used to accommodate the air pump 32, the individual exhalation imprinting sampling module 36, the aerosol nozzle 311 and the gas solenoid valve 35.

The exhalation imprinting operation cabin 3 will be further introduced below.

The exhalation imprinting operation cabin 3 includes: a top cover 30, a bottom cover 313, two curved sliding doors 31, a support frame 310 and a support disk 39. The air pump 32 penetrates the top cover 30 and is connected to the outlet of the organic steam micro-injection module 1; a second end of the aerosol nozzle 311 penetrates the bottom cover 313; the top cover 30 and the bottom cover 313 are embedded with an inner track and an outer track; the two curved sliding doors 31 are respectively disposed between the top cover 30 and the bottom cover 313, and the two curved sliding doors 31 slide along the inner track and the outer track through a roller, respectively; two ends of the support frame 310 are connected to the top cover 30 and the bottom cover 313, respectively; the support disk 39 is disposed between the top cover 30 and the bottom cover 313, and the support disk 39 penetrates the support frame 310. The curved sliding door 31 has a half-moon shape and is provided with a roller, and the two curved sliding doors 31 with different curvatures may slide at any angle along the inner tracks of the top cover 30 and the bottom cover 313 and the outer tracks of the top cover 30 and the bottom cover 313, respectively, which may facilitate an experimental operation in the exhalation imprinting operation cabin 3.

Figure 10:
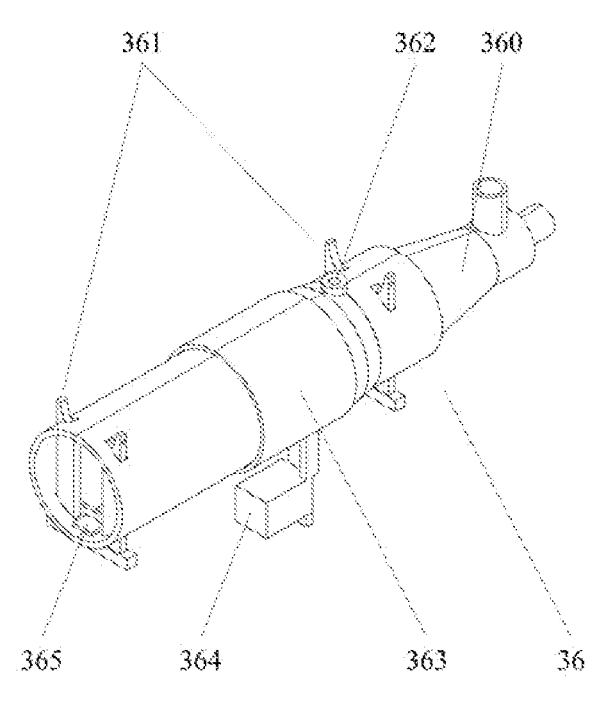
FIG. 10 is a schematic structural diagram of an individual exhalation imprinting sampling module.
Figure 11:
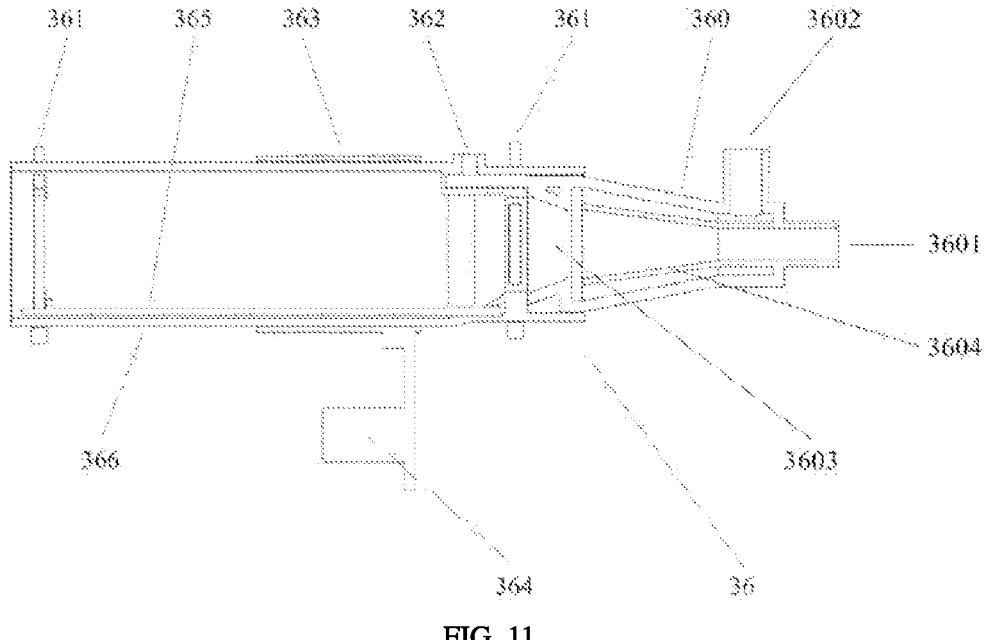
FIG. 11 is a schematic diagram of a cross-sectional structure of an individual exhalation imprinting sampling module.

As shown in FIG. 10 and FIG. 11, the individual exha-lation imprinting sampling module 36 includes: a mask 360, an air inlet 3601, an air outlet 3602, an experimental animal oro-nasal interface 3603, a main pipe 366 and a hygroscopic strip plate 365.

In an alternative embodiment, a cross section of the mask 360 has a double-layer lumen tube structure. The air inlet 3601 is in communication with a first end of an inner lumen tube 3604 of the mask 360. The air outlet 3602 is in communication with an outer wall surface of an outer lumen tube of the mask 360. The experimental animal oro-nasal interface 3603 is a hollow conical tube of the mask 360 in contact with a head of the experimental animal. It should be noted that the experimental animal oro-nasal interface 3603 is not directly connected to the inner lumen tube 3604 of the mask 360. When the head of the experimental animal is inserted into the oro-nasal interface 3603, an experimental animal oro-nasal end extends out of the oro-nasal interface 3603 and faces the inner lumen tube 3604 of the mask. Air inside the double-layer lumen tube of the mask 360 may flow unidirectionally from the air inlet 3601 toward the air outlet 3602.

In an alternative embodiment, the mask 360 may be spliced with the main pipe 366, and a protrusion at the bottom of the mask 360 faces a slot of the main pipe 366, and the slot is in communication with a fixing screw hole 362. The mask 360 may be fixed with the main pipe 366 by fastening the protrusion at the bottom of the mask 360 through the fixing screw hole 362.

In an alternative embodiment, a limit latch 361 may be inserted into an opening of the main pipe 366 close to the mask 360. Use of the limit latch 361 together with the mask 360 may restrict a free movement of the head of the experimental animal. An opening size of the limit latch 361 is less than a measured head size of the experimental animal and greater than a neck size of the experimental animal, which may ensure that a compression of an upper respiratory tract of the experimental animal is avoided when a head movement is restricted. A tip end of the limit latch 361 has a hemispherical protrusion, which may prevent the limit latch 361 from slipping from the transparent pipe 366.

In an alternative embodiment, a limit latch 361 may be inserted into an opening of the main pipe 366 far away from the mask 360 so as to ensure that the experimental animal may not escape from the transparent pipe 366 even if the experimental animal leaves the mask during the operation. In a specific embodiment, those skilled in the art may specifically customize an inner diameter of the main pipe 366 according to a body shape of the experimental animal, so as to achieve an effect of preventing the experimental animal from turning around, which will not be specifically limited. Therefore, a possibility of the experimental animal escaping from the main pipe 366 may be further reduced.

For the hygroscopic strip plate 365, a first end of the hygroscopic strip plate 365 is spliced with a first end of the main pipe 366, and a second end of the hygroscopic strip plate 365 is fixed by the limit latch 361 inserted at the opening of the main pipe 366 far away from the mask 360, and the hygroscopic strip plate 365 is opposite to a ventral surface of the experimental animal, which is used to absorb urine and keep the inside of the main pipe 366 dry.

In an alternative embodiment, the individual exhalation imprint sampling module further includes: a camera fixing ring 363, a camera 364 and a breath video collector 44.

The camera fixing ring 363 may be sleeved on the main pipe 366, and a bottom portion of the camera fixing ring 363 is connected to the camera 364. A lens of the camera 364 points toward a chest and abdomen of the experimental animal to shoot a breath video, and the camera 364 is connected to the breath video collector 44 through a data line so as to receive the breath video of the experimental animal shot by the camera 364. After a further image processing and machine vision analysis, video data stored in the breath video collector 44 may also be used to reflect a breath physiological state of the experimental animal in the exhalation imprinting.

Further, in order to better shoot the breath video of the experimental animal, the main pipe 366, the hygroscopic strip plate 365 and the camera fixing ring 363 may all have transparent structures, such as a fully transparent structure, a partially transparent structure in which a main shooting position is transparent, etc.

In an alternative embodiment, the system of measuring exhalation metabolism further includes: a multifunctional ejector 312, where a first end of the multifunctional ejector 312 is connected to the second end of the aerosol nozzle 311, and a second end of the multifunctional ejector 312 is connected to the air outlet of the zero-level air purifier 42.

Figure 14:
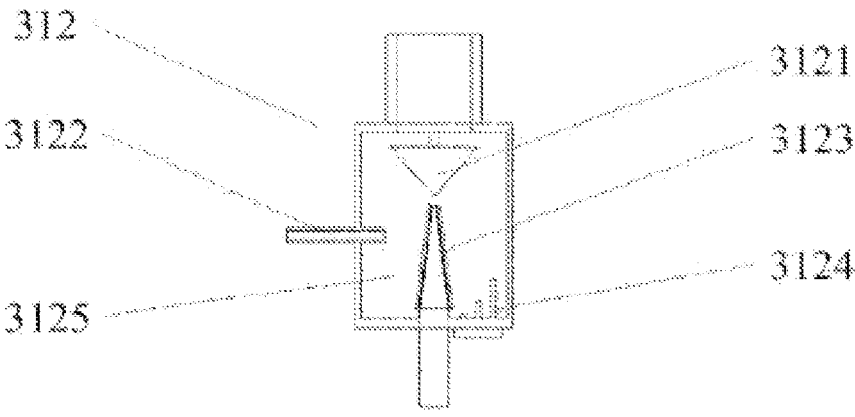
FIG. 14 is a schematic structural diagram of a multifunctional ejector.

The multifunctional ejector 312 will be further introduced below, as shown in FIG. 14.

The multifunctional ejector 312 includes: an ejector chamber 3125, a liquid level sensor 3124, a gas-liquid interface 3122, a two-phase nozzle 3123 and a turbulence cone 3121. The injector chamber 3125 is connected to a first end of the gas-liquid interface 3122. A second end of the gas-liquid interface 3122 is respectively connected to the organic steam micro-injection module 1 and/or an external supplementary device. After the gas-liquid interface 3122 is connected to the organic steam micro-injection module 1, the gas-liquid interface 3122 may be used for both an inhalation exposure of the organic steam and an internal standard quantification of a target metabolite. Here, the external supplementary device may be selected from a gas cylinder, a liquid replenishment device, etc. When the gas-liquid interface 3122 introduces a solution or a turbid liquid into the injector chamber 3125, the liquid level sensor 3124 is connected to an external liquid replenishment device to control a liquid replenishment process. A first end of the two-phase nozzle 3123 extends into the ejector chamber 3125, and a second end of the two-phase nozzle 3123 is connected to the air outlet of the zero-level air purifier 42. The two-phase nozzle 3123 pneumatically atomizes a liquid in the ejector chamber 3125 and generates an aerosol. The turbulence cone 3121 is disposed inside the ejector chamber 3125, and the turbulence cone 3121 is disposed opposite to the first end of the two-phase nozzle 3123 to impact the aerosol inside the ejector chamber 3125, which may eliminate particles with a relatively large particle size in the aerosol to facilitate the inhalation exposure. The two-phase nozzle 3123 cooperates with the turbulence cone 3121 to dilute and mix the organic steam, gas or aerosol in the ejector chamber 3125.

Figure 12:
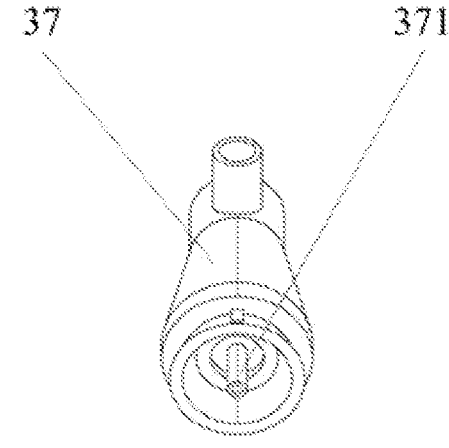
FIG. 12 is a schematic structural diagram of an external standard module.

In an alternative embodiment, the system of measuring exhalation metabolism further includes: an external standard module 37. The external standard module 37 is used to simulate an exhalation process of the experimental animal and an external standard quantification of the target metabolite. As shown in FIG. 12, the external standard module 37 is connected to the second end of the liner 33. An organic steam interface 371 of the external standard module 37 is connected to the air outlet of the zero-level air purifier 42.

In an alternative embodiment, the system of measuring exhalation metabolism further includes: an air background module 38. The air background module 38 is used to detect an air background in the system of measuring exhalation metabolism. The air background module 38 is connected to the second end of the liner 33.

So far, embodiments of the present disclosure have been described in detail with reference to the accompanying drawings. It should be noted that implementations not shown in the accompanying drawings or described in the text of the specification are all known to those skilled in the art and have not been described in detail. In addition, the above-mentioned definitions of elements and methods are not limited to the specific structures, shapes or methods mentioned in the embodiments, and may be simply changed or replaced by those skilled in the art.

Based on the above-mentioned descriptions, those skilled in the art should have a clear understanding of the system of measuring exhalation metabolism in the present disclosure.

In summary, the present disclosure provides a system of measuring exhalation metabolism that may synchronously operate inhalation exposure and exhalation imprinting on the experimental animal, which may solve the current problem that it is difficult to combine the inhalation exposure with the exhalation imprinting in real time. In the researches of biology, medicine, pharmacy and other fields, the real-time response of the exhalation metabolome change to the inhalation exposure plays an irreplaceable role in revealing an immediate health effect of an exogenous substance entering an organism through inhalation.

The above-mentioned specific embodiments have described in detail the objectives, technical solutions and advantages of the present disclosure. It should be understood that the above are only specific embodiments of the present disclosure and are not intended to limit the present disclosure. Any modifications, equivalent substitutions, improvements, and the like made within the spirit and scope of the present disclosure shall be included in the scope of protection of the present disclosure.

What is claimed is:

1. A system of measuring exhalation metabolism, comprising:

an organic steam micro-injection module, wherein an organic steam is output from an outlet of the organic steam micro-injection module;

an air pump, wherein a first end of the air pump is connected to the outlet of the organic steam micro-injection module, and a second end of the air pump is connected to a first end of a liner;

an individual exhalation imprinting sampling module, wherein an experimental animal is placed inside the individual exhalation imprinting sampling module, an air outlet of the individual exhalation imprinting sampling module is connected to a second end of the liner, and a stirrer adsorption extraction rod is provided inside the liner to sample an exhalation metabolite of the experimental animal;

an aerosol nozzle radially provided with at least one nozzle interface, wherein the nozzle interface is connected to the air outlet of the individual exhalation imprinting sampling module;

a gas solenoid valve connected to a first end of the aerosol nozzle;

a zero-level air purifier, wherein an air outlet of the zero-level air purifier is connected to an air inlet interface of the gas solenoid valve and/or an air inlet of the individual exhalation imprinting sampling module; wherein the gas solenoid valve is configured to control zero-level air output by the zero-level air purifier to enter the individual exhalation imprinting sampling module and synchronously block an inhaled exposed substance from entering the individual exhalation imprinting sampling module; and an automatic solvent desorption module configured to detect the exhalation metabolite collected by the stirrer adsorption extraction rod.

2. The system of measuring exhalation metabolism according to claim 1, further comprising:

an external standard module connected to the second end of the liner, wherein the external standard module is configured to simulate an exhalation process of the experimental animal and an external standard quantification of a target metabolite; wherein an organic steam interface of the external standard module is connected to the air outlet of the zero-level air purifier.

3. The system of measuring exhalation metabolism according to claim 1, further comprising:

an air background module connected to the second end of the liner, wherein the air background module is configured to detect an air background in the system of measuring exhalation metabolism.

4. The system of measuring exhalation metabolism according to claim 1, wherein the individual exhalation imprinting sampling module comprises:

a mask, wherein a cross section of the mask has a double-layer lumen structure;

the air inlet in communication with a first end of an inner lumen tube of the mask;

the air outlet in communicated with an outer wall surface of an outer lumen tube of the mask;

an experimental animal oro-nasal interface, wherein a first end of the experimental animal oro-nasal interface is connected to a second end of the mask; a head of the experimental animal extends into a second end of the experimental animal oro-nasal interface and is opposite to a second end of the inner lumen of the mask;

a main pipe, wherein a first end of the main pipe is spliced with the second end of the mask; and a hygroscopic strip plate, wherein a first end of the hygroscopic strip plate is spliced with the first end of the main pipe, a second end of the hygroscopic strip plate is connected to a second end of the main pipe through a limit baffle, and the hygroscopic strip plate is opposite to a ventral surface of the experimental animal.

5. The system of measuring exhalation metabolism according to claim 4, wherein the main pipe and the hygroscopic strip plate have a transparent structure, and the individual exhalation imprinting sampling module further comprises:

a camera fixing ring sleeved on an outer wall of the main pipe;

a camera connected to the camera fixing ring, wherein a lens of the camera is opposite to the ventral surface of the experimental animal; and an exhalation video collector configured to receive a breath video of the experimental animal shot by the camera.

6. The system of measuring exhalation metabolism according to claim 1, further comprising:

a multifunctional ejector, wherein a first end of the multifunctional ejector is connected to a second end of the aerosol nozzle, and a second end of the multifunctional ejector is connected to the air outlet of the zero-level air purifier; wherein the multifunctional ejector comprises:

an ejector chamber connected to a first end of a gas-liquid interface;

the gas-liquid interface, wherein a second end of the gas-liquid interface is connected to the organic steam micro-injection module;

a two-phase nozzle, wherein a first end of the two-phase nozzle extends into the ejector chamber, a second end of the two-phase nozzle is connected to the air outlet of the zero-level air purifier, and the two-phase nozzle is configured to pneumatically atomize a liquid in the ejector chamber and generate an aerosol; and a turbulence cone disposed inside the ejector chamber, wherein the turbulence cone is disposed opposite to the first end of the two-phase nozzle so as to impact the aerosol inside the ejector chamber.

7. The system of measuring exhalation metabolism according to claim 1, wherein the organic steam micro-injection module comprises:

an injector, wherein a cavity of the injector is filled with the organic steam;

a thermostatic slot seat, wherein the injector is inserted into a slot body of the thermostatic slot seat;

a guide rod, wherein a push rod is fixed on the thermostatic slot seat;

a stress plate sleeved on the guide rod; and a drive device configured to drive the stress plate to move along the guide rod toward the thermostatic slot seat, wherein the stress plate is configured to press the push rod of the injector, so that the organic steam is output through an injection port of the injector.

8. The system of measuring exhalation metabolism according to claim 1, further comprising: an exhalation imprinting operation cabin configured to accommodate the air pump, the individual exhalation imprinting sampling module, the aerosol nozzle and the gas solenoid valve; wherein the exhalation imprinting operation cabin comprises:

a top cover, wherein the air pump penetrates the top cover and is connected to the outlet of the organic steam micro-injection module;

a bottom cover, wherein a second end of the aerosol nozzle penetrates the bottom cover, wherein the top cover and the bottom cover are embedded with an inner track and an outer track;

two curved sliding doors respectively disposed between the top cover and the bottom cover, wherein the two curved sliding doors slide along the inner track and the outer track through a roller, respectively;

a support frame, wherein two ends of the support frame are connected to the top cover and the bottom cover, respectively; and a support disk disposed between the top cover and the bottom cover, wherein the support disk penetrates the support frame.

9. The system of measuring exhalation metabolism according to claim 1, wherein the automatic solvent desorption module comprises:

an accommodating cavity, two smooth electromagnetic rods and a transmission rubber rod, wherein the transmission rubber rod is disposed between the two smooth electromagnetic rods, and two ends of the transmission rubber rod and the smooth electromagnetic rod penetrate the accommodating cavity, respectively;

a sample bottle horizontally placed between the two smooth electromagnetic rods, wherein a solvent and the stirrer adsorption extraction rod are provided inside the sample bottle, and the stirrer adsorption extraction rod is provided with a magnetic core;

a stepping motor configured to electromagnetically drive the smooth electromagnetic rod to rotate; and a desorption process controller configured to control a rotation direction, a rotation speed and rotation time of the sample bottle.

10. The system of measuring exhalation metabolism according to claim 9, wherein the automatic solvent desorption module further comprises:

a sample bottle magnetic pipe rack configured to vertically insert the desorbed sample bottle into the sample bottle magnetic pipe rack; wherein two ends of each sample bottle magnetic pipe rack are provided with magnetic fields with opposite magnetic field directions, so that the stirrer adsorption extraction rod inside the sample bottle is attached to an inner wall of the sample bottle.

* * * * *